United States Patent [19]

Gordon

[11] Patent Number: 4,994,014
[45] Date of Patent: Feb. 19, 1991

[54] PROCESS FOR TREATING DISEASED CELLS INCLUDING THE STEP OF RAISING THE SUBJECTS BLOOD OXYGEN LEVEL

[76] Inventor: Robert T. Gordon, 4936 W. Estes, Skokie, Ill. 60077

[21] Appl. No.: 224,144

[22] Filed: Jul. 26, 1988

[51] Int. Cl.$^5$ .............................................. A61N 2/02
[52] U.S. Cl. ................................ 600/13; 128/205.26; 128/804; 424/9
[58] Field of Search ................... 128/804, 205.26, 399; 424/9; 600/9, 13

[56] References Cited

U.S. PATENT DOCUMENTS

| | | | |
|---|---|---|---|
| 4,303,636 | 12/1981 | Gordon | 424/9 X |
| 4,359,453 | 11/1982 | Gordon | 424/9 X |
| 4,569,836 | 2/1986 | Gordon | 424/9 X |

*Primary Examiner*—Ruth S. Smith
*Attorney, Agent, or Firm*—Banner, Birch, McKie & Beckett

[57] ABSTRACT

A process for treating diseased cells in the living tissue of a subject. A solution of ferric oxyhydroxide or other intracellular chemically-generated, energy particles is intravenously injected into the subject. After the particles have been intracellularly absorbed by the diseased cells, the oxygen level in the subject's blood is raised, as by subjecting him to hyperbaric air or oxygen. This increases the rate of the intracellular absorption of oxygen by the diseased cells. This oxygen absorption then together with the intracellularly-absorbed particles increase the rate of oxidation and metabolism of the particles, and thereby raise the subject's intracellular energy. The intracellular production of interleukins and other activators, such as interferons and prostaglandins, is thereby stimulated, and these interleukins and other activators destroy the diseased cells wherever they may be in the subject. This process can be enhanced by then applying an alternating electromagnetic field tuned to a resonant frequency to the subject.

50 Claims, 4 Drawing Sheets

DETERMINATION OF RESONANT FREQUENCIES
OF ATHEROSCLEROTIC TISSUE, CANCER CELLS
OR DISEASED CELLS VS. NORMAL CELLS OR
TISSUE.

↓

MODIFICATION, IF NECESSARY, BY THE
INTRACELLULAR ABSORPTION OF MINUTE
PARTICLES IN ATHEROSCLEROTIC TISSUE,
CANCER CELLS OR DISEASED CELLS.

← AFFECT BY AN EXTERNAL ELECTROMAGNETIC FIELD.

↓

PRODUCTION OF IL-1, IL-2 OR
INTERLEUKIN-LIKE SUBSTANCES

← AFFECT BY AN EXTERNAL ELECTROMAGNETIC FIELD

↓

ALTERATION OF CELL FUNCTION DUE TO
ACTION OF INTERLEUKIN-LIKE SUBSTANCES.

FIG. 3

INTRODUCING INTO LIVING TISSUE
INTRACELLULAR, CHEMICALLY-GENERATED
ENERGY PARTICLES

SELECTIVELY DIRECTING THE
INTRODUCED PARTICLES TO THE
DISEASED CELLS

ALLOWING THE PARTICLES TO
BE INTRACELLULARLY ABSORBED
BY THE DISEASED CELLS

RAISING THE LEVEL OF OXYGEN
IN THE BLOOD OF THE SUBJECT

PRODUCTION OF INTERLEUKIN AND
OTHER ACTIVATORS

DESTRUCTION OF DISEASED CELLS

PROCESS FOR TREATING DISEASED CELLS INCLUDING THE STEP OF RAISING THE SUBJECTS BLOOD OXYGEN LEVEL

FIELD OF THE INVENTION

This is a continuation-in-part of co-pending application Ser. No. 07/197,302, filed May 23, 1988, now abandoned, which is a continuation-in-part of application Ser. No. 06/916,557, filed Oct. 8, 1986, now abandoned, and also of co-pending application Ser. No. 07/082,561, filed Aug. 7, 1987, now abandoned, which in turn is a divisional of the abandoned ,'557 application. The entire contents of all of these applications are hereby incorporated by reference in their entirety.

The present invention relates primarily to processes for treating diseased cells. It also relates to processes for producing interleukin-2 (IL-2) and interleukin-like substances. It further relates to processes for treating cancer and other diseases in living tissues, and is an extension of the technologies described in U.S. Pat. Nos. 4,106,488, 4,136,683, 4,622,952, and 4,622,953. The entire contents of these four patents are hereby incorporated by reference. More particularly, the present invention relates to methods for achieving biophysical alterations in the intracellular structure of cells. These biophysical alterations include thermal changes, the stimulation of the intracellular production of interleukins, the modulation of their activities, and the treatment of cancer and other diseases by intracellularly killing the cancer and/or diseased cells without injuring the normal cells. The present invention further relates to processes for modulating the interaction of interleukin-2 (IL-2) and the cells to be activated, and for modulating the interaction of natural killer (NK) cells and target cells in living tissue.

BACKGROUND OF THE INVENTION

There are presently a number of methods and techniques for the treatment of cancer and other diseases, among which may be included radiation therapy, chemotherapy, immunotherapy, and surgery. The common characteristic of all of these techniques as well as any other presently known techniques is that they are extracellular in scope; that is, the cancer or diseased cell is attacked and attempted to be killed through application of a killing force or medium outside of the cell. The only known exceptions are U.S. Pat. Nos. 4,106,488, 4,622,952, and 4,622,953, and this invention is an extension of the technologies described therein.

The extracellular approach however is less effective than the intracellular approach because of the difficulties of penetrating the outer membrane of the cancer or diseased cell that is composed of two protein layers with a lipid layer in between. Of even greater significance is that in order to overcome the protection afforded the cell by the cell membrane in any extracellular technique, the attack on the cancer or diseased cells must be of such intensity that considerable damage is caused to the normal cells resulting in severe side effects upon the subject. These side effects have been found to limit considerably the effectiveness and usefulness of these extracellular treatments.

A safe and effective cancer and disease treatment has been the goal of investigators for a substantial period of time. Such a technique to be successful in the destruction of the cancer or diseased cells must be selective in its effect upon the cancer or diseased cells and produce no irreversible damage to the normal cells. In sum, cancer and/or disease treatment must selectively differentiate cancer or diseased cells from normal cells and must selectively weaken or kill the cancer or diseased cells without affecting the normal cells.

It has been known that there are certain physical differences that exist between cancer and other diseased cells and normal cells. One primary physical difference is the temperature differential characteristics between the cancer and other diseased cells and the normal cells. Cancer cells and other diseased cells, because of their higher rates of metabolism, have higher resting temperatures than those of normal cells. In the living cell, the normal temperature of the cancer and other diseased cells is known to be 37.5° Centigrade, while that of the normal cell is 37° Centigrade. Another physical characteristic that differentiates the cancer and other diseased cells from the normal cells is that cancer and other diseased cells die at lower temperatures than do normal cells. The temperature at which a normal cell will be killed and thereby irreversibly will be unable to perform normal cell functions is a temperature of 46.5° Centigrade, on the average. The cancer and other diseased cells, in contrast, are killed at the lower temperature of 45.5° Centigrade. Thus, the temperature elevation increment necessary to cause death in the cancer or diseased cell is determined to be at least approximately 8.0° Centigrade, while the normal cell can withstand a temperature increase of at least 9.5° Centigrade.

It is known, therefore, that with a given precisely controlled increment of heat, the cancer or diseased cells can be selectively destroyed without injuring the normal cells. On the basis of this known differential in temperature characteristics, a number of extracellular attempts have been made to treat cancer and other diseases by heating the cancer or diseased cells in the body. This concept of treatment is referred to as hyperthermia. To achieve these higher temperatures in the cancer and diseased cells, researchers have attempted a number of methods including inducing high fevers, utilizing hot baths, diathermy, applying hot wax, and even the implantation of various heating devices in the area of the cancer or diseased cells.

Presently, none of the various known approaches to treat cancer and other diseases has been truly effective, and all have the common characteristic of approaching the problem by treating the cancer or diseased cells extracellularly. The only known exceptions are the techniques disclosed in the previously mentioned 4,106,488, 4,622,952 and 4,622,953 patents. The outer membrane of the cancer or diseased cell being composed of lipids and proteins is a poor thermal conductor, thereby making it difficult for heat which is applied by external means to penetrate into the interior of the cell where the intracellular temperature must be raised to effect the death of the cell. If, through the extracellular approaches of the prior hyperthermia techniques, the temperatures were raised sufficiently to effect an adequate intracellular temperature to kill the cancer or diseased cells, many of the normal cells adjacent the application of heat would be destroyed as well.

It has been known that the nuclei of cancer and other diseased cells and the nuclei of normal cells possess some differences. The alterations which occur in a cell to produce malignancy or disease either take place in, or are transmitted to, the nucleus. This is evident by the fact that the cells produced by the tumor and other diseased cells multiplication possess the same characteristics as the original tumor or diseased cells.

A large amount of work has been done "in vitro" concerning the magnetic resonant frequencies of cancer and other diseased cells as compared to those of normal tissues. Differences have been attributed to differences in the amount of water present in the cancer or diseased cells and the way in which the water molecules are ordered. A key to this process lies in the nuclear differences, including energy changes characteristic of structural and conformational changes in the deoxyribonucleic acid and the histones of the nucleus, including their relationship, resulting in differential resonant frequencies for the cancer or other diseased cells from the normal cells.

A further key to this process is the additional changes in intracellular biophysical characteristics which occur in this process. Included in these changes is the intracellular production of interleukins and other activators, such as interferons and prostaglandins. The production of interleukins, interleukin-like substances such as interleukin-1 (IL-1) and IL-2, and other activators can be triggered by alterations or changes in the cell's environment.

Unfortunately even if the interleukins or activators are synthesized and subsequently injected intravascularly into a subject, their effectiveness is limited due to the loss of time and specificity between injection into the subject and the time when the synthesized or isolated interleukins reach the cellular level where their effectiveness is required. Interleukins are most effective when stimulated intracellularly and their peak effectiveness and potential are utilized on the specific sites in the subject.

Additionally, this invention is secondarily directed to techniques for modulating the interaction of IL-2 and the cell to be activated and for modulating the interaction of NK cells and target cells. Prior art modulation techniques usually require that interleukin or some chemical substances be physically introduced into the subject. These substances however are often destroyed or altered, due to the body's metabolism activity, prior to reaching the cells to be changed. Therefore, these prior approaches are limited in their ability to modulate the interaction of interleukins and the cells to be activated.

This invention further relates to processes for treating atherosclerotic lesions. Present treatments involve surgery, balloon angioplasty or lasers. Surgery is of course an invasive procedure and recurrence often occurs in the grafted vessels. Balloon angioplasty involves the use of cardiac catheterization to place a guide wire and then a balloon in the lesion to dilate the lesion. Unfortunately, this is also invasive and requires cardiac catheterization with a significant recurrence rate and the danger of requiring immediate emergency surgery. The use of lasers to burn the lesions has been tried along with utilizing certain wavelengths of light in combination with porphyrins taken up by the plaque. The porphyrins which are taken up by the plaque respond to a certain wavelength. However, in order to get the light to the coronary artery, the laser must be introduced via catheterization which also is an invasive procedure.

OBJECTS OF THE INVENTION

It is therefore a principal object of the present invention to provide a process for selectively destroying cancer and other diseased cells by achieving biophysical alterations in the intracellular structure of the cancer and other diseased cells, such as atherosclerotic and infectious cells, while producing no significant effects upon the normal cells. The biophysical alterations include thermal changes, the stimulation of the intracellular production of interleukins and other activators, and the modulation of their activities and those of the NK cells created.

Another object of the present invention is to provide an improved process for treating diseased cells, and particularly atherosclerotic lesions, which process is non-invasive, does not involve the risks of catheterization, and avoids the risks of damage by catheter and laser systems.

Other objects and advantages of the present invention will become apparent to those persons having ordinary skill in the art to which the present invention pertains from the foregoing description taken in conjunction with the accompanying drawings.

SUMMARY OF THE INVENTION

A process for treating diseased cells in the living tissue of a subject is provided herein. A solution of ferric oxyhydroxide or other intracellular chemically-generated, energy particles are intravenously injected into the subject. After the particles have been intracellularly absorbed by the diseased cells, the oxygen level in the subject's blood is raised, as by subjecting him to hyperbaric oxygen or hyperboric air, to thereby increase the rate of the intracellular absorption of oxygen by the diseased cells. This oxygen absorption then together with the intracellularly-absorbed particles increase the rate of oxidation and metabolism of the particles, and thereby raise the subject's intracellular energy. The intracellular production of interleukins and other activators, such as interferons and prostaglandins, is thereby stimulated, and these interleukins and other activators destroy the diseased cells wherever they may be in the subject. This process can be enhanced by then applying to the subject an alternating electromagnetic field tuned to a resonant frequency of the diseased cells.

A treatment of cancer and other diseases by the application of external electromagnetic energy capable of achieving biophysical alterations in the intracellular structure of cancer and other diseased cells in living tissue is also herein provided. These biophysical alterations include thermal changes, the stimulation of intracellular production of interleukins, interleukin-like substances and other activators and the modulation of their activities. (Interleukin-like substances are well-known in the scientific community and the term is used often in scientific terminology; IL-1 and IL-2 are examples thereof.) The process accomplishes these biophysical alterations by tuning external electromagnetic energy to at least one resonant energy absorption frequency of the intracellular structure of the selected cells. Alternatively, the field can be tuned to the frequency which has been calculated to be closest to the resonant frequencies of the cancer or diseased cells and furthest from the resonant frequencies of the normal cells. The range of frequencies will typically vary from 50 kHz to 100 MHz. As an example, the resonant frequencies of normal cells may be 800 kHz, 5 MHz, 9 MHz, while that of cancer cells to produce IL-2 is 100 kHz. Consequently, a frequency of 100 kHz would be utilized to induce the production of IL-2 and to affect the cancer cells. Similarly, the selected field strengths depend on which cells are to be affected and the ultimate alteration desired.

The process may be further enhanced by the intracellular absorption of selected materials designed to alter the magnetic susceptibility and therefore the resonant energy absorption frequency of the intracellular structure. The biophysical differences between diseased cells and normal cells make possible the selective absorption of materials thereby enhancing the differences in magnetic susceptibilities between diseased cells and normal cells resulting in an increased capability of selective energy absorption by the diseased cells. The particle material similarly chosen is based upon the cells involved and the desired change(s) to be produced.

This technology has diagnostic applications in the detection of cancer and other diseased cells in combination with the use of differential resonant frequencies, magnetic resonance and electron spin resonance techniques. The process has application in the treatment of a wide range of diseases at the cellular level, particularly in the field of cancer where this mode of affecting the thermal characteristics and of stimulating the intracellular production of interleukins and other activators and modulating their activities will be effective in the selective destruction of cancer cells without injuring the normal cells and tissues. This modulation, for example, might affect the intensity and/or the duration of the activation or interaction.

DETAILED DESCRIPTION OF PREFERRED EMBODIMENTS OF THE INVENTION

The present invention achieves a precise increment of heat rise within the cancer cell and within the cytoplasm. The thermal barrier that characteristically exists as the outer membrane or cell wall of the cell is now utilized to retain the heat produced within the cell rather than, as in the past, to prevent any heat build-up within the cell. On the basis of the cell resting temperatures and the temperature necessary to produce cell death, the increment that the cell temperature must be raised to cause the cell death is critical. As previously stated, in the normal cell the temperature rise is 9.5° Centigrade, while in the cancer and other diseased cells the temperature rise is approximately 8.0° Centigrade. Thus, any temperature rise in the cancer or other diseased cell or in the normal cell that is at least 8.0° Centigrade and not more than 9.5° Centigrade above the normal cell temperature results in the selective destruction of the cancer cell without any harmful effects to the normal cell.

In accordance with the present invention, a number of approaches can successfully achieve the end result of an intracellular heat rise and an intracellular destruction of the cancer and other diseased cells. In its simplest and broadest aspect, the invention contemplates the use of the differential resonant frequencies of cancer, other diseased cells and normal cells to allow significant energy absorption into the cancer and other diseased cells at their specific resonant frequency while allowing very little energy absorption into the normal cells. The nuclei of the cancer or other diseased cells (the DNA, histones, etc.) besides often being different in content, usually differ in conformation and binding from the nuclei of normal cells (the DNA, histones, etc.). These differences contribute to the variance in the resonant frequencies between the structures in cancer cells and in normal cells. This difference between the cancer and other diseased cells and the normal cells being nuclear in origin is transmitted to the daughter cancer and other diseased cells formed by cell division and explains the daughter cells' propensity towards malignancy and disease.

A tuning fork will resonate, absorbing energy, from sound produced by another tuning fork of the same pitch or frequency twenty or thirty feet away. If various structures are placed within the effective range of a high frequency electromagnetic field, the structures having the same resonant frequency as the electromagnetic field will be the ones to best absorb energy from that field. Therefore, by placing the subject within the effective range of the high frequency electromagnetic field and by tuning the frequency of this field to the specific resonant frequency of the cancer or diseased cells, the cancer or diseased cells will then absorb energy from this electromagnetic field resulting in the raising of their intracellular temperature and the affecting of their biophysical properties so as to thereby selectively destroy these cells without affecting the normal cells.

Computerized axial tomography techniques can be combined with an electromagnetic field generator and detection receiver sensing techniques to obtain three-dimensional data on specific point resonant energy absorption at a range of frequencies. The fact that the resonant frequency of the cancer cells is different from that of the normal cells and that of other diseased cells is different from that of the normal cells serves to locate the cancer and other diseased cells.

One possible method provides a large helical coil, places the subject within that coil and energizes the entire coil using a high frequency generator so that the entire subject is within the effective range of the electromagnetic field thereby produced. The frequency of this electromagnetic field is selected as the one closest to the resonant frequencies of the cancer or other diseased cells and furthest from those of the normal cells. The cancer and other diseased cells will absorb energy at their resonant frequency and will be destroyed intracellularly while the normal cells are unharmed.

This destruction of the cancer and other diseased cells can be monitored by repeating the first part after completion of the second in order to monitor the destruction of the cancer and other diseased cells. This destruction can be monitored by observing the absence of cells which absorb energy at the resonant frequency of the cancer and other diseased cells.

This technology has application for example in the treatment of atherosclerosis. Research work by the inventor and studies in the literature suggest that the development of atherosclerotic lesions is in many ways similar to tumor formation with the multiplication of a single cell line and the proliferation of smooth muscular cells (the monoclonal theory). These proliferating smooth muscle cells along with the deposition of cholesterol allow the components of the atherosclerotic plaque to have resonant frequencies different from those of the normal intimal wall. The magnetic resonant frequencies of lipids in bilayers and membranes as well as of phospholipids in relation to membrane permeability (which of course is very important to this discussion of atherosclerosis) have been studied. Membrane perturbations by physical agents can actually be followed using electron spin probe analysis. Using selective irradiation of the specimen in switched magnetic field gradients, blood flow in a vessel can be measured due to the different spin characteristics of the new polarized blood entering a specific region of the vessel. Studies by the inventor, along with studies of others found in the literature, illustrate the changes in the newly-formed atherosclerotic plaques.

Therefore, by performing a three-dimensional scan utilizing magnetic resonant sensing techniques, the areas of atherosclerotic lesions may be identified. Subsequently, by subjecting the subject to the frequency closest to the resonant frequency of the atherosclerotic lesions, the lesions may be destroyed due to the absorption of energy, without affecting the normal vessel wall whose cells respond to a different set of frequencies.

The uptake of particles by tumors and atherosclerotic plaques in certain stages of their formation has been demonstrated. Magnetic resonant sensing techniques may be utilized to characterize the magnetic parameters of the structures. Electron spin probe analysis has been used to detect membrane perturbation by physical agents. By allowing the tumor or atherosclerotic plaque to take up the particles, be they ferromagnetic, paramagnetic, or diamagnetic, the process of determining the resonant frequencies of the cancer cells or the atherosclerotic lesions and of energy absorption at the desired resonant frequency may thereby be enhanced.

The production of interleukins in the subject is caused normally by a number of stimuli, such as trauma, infection, and drugs. The interleukin then acts to create a defense to this stimulus. As an example, IL-2 when stimulated causes certain cells, i.e. lymphocytes, monocytes, and macrophages, to transform into NK cells. These NK cells are then able to be cytotoxic and to destroy the cancer and other diseased cells. The activation of these cells by IL-2 is linked to receptors for IL-2 and also for transferrin on the cells. Consequently by using particles attached to transferrin the ability of the IL-2 to activate the potential NK cell can be modulated. This modulation can be enhanced even further with the use of an alternating electromagnetic field.

The receptors for IL-2 and transferrin are related on the cell surface. Examples of recent articles connecting IL-2 receptors and transferrin receptors on the membrane are "A Transferrin Receptor Antibody Represents One Signal for the Induction of IL 2 Production by a Human T Cell Line," *The Journal of Immunology*, Vol. 136, No. 2, Jan. 15, 1986, pgs. 532–538; "The Role of Transferrin in Natural Killer Cell and IL-2-Induced Cytotoxic Cell Function," *Cellular Immunology* 97, pgs. 121–130 (1986); and "The Regulation by Low-Density Lipoproteins of the Activation of Oxidative Enzyme-Primed Lymphocytes is Governed by Transferrin," *Cellular Immunology* 108, pgs. 378–395 (1987). The entire contents of each of these articles are hereby incorporated by reference. Thus, using the process described herein, the transferrin receptor can be affected through the use of the particle system and the external electromagnetic field. This ability to modulate the activity of the transferrin receptor also allows modulation of the IL-2 receptor and subsequent transformation of the cell, since the transferrin receptors and IL-2 receptors are closely interrelated.

In a similar manner the ability of NK cells to be cytotoxic depends on their recognition of the cancer or other diseased cells. This recognition has also been shown to be linked to the transferrin receptors on the tumor or other diseased cells. Therefore the same procedure can be used to modulate the activity between the NK cells and the target cells. "Modulation of their activity" implies that through the use of the processes described herein cellular and intracellular events can be affected. The production of IL-2, and the ability to modulate the effect of IL-2 on cells to activate them to NK cells are examples thereof. For both of these examples, the production of IL-2 and the affect on its function can be controlled through the processes described herein.

In summary, the processes herein can be used:

(1) to stimulate the production of interleukins and/or interleukin-like substances or activators;

(2) to modulate the activation of potential NK cells and the effect of IL-2 on the cells; and (3) to modulate the interaction of the NK cells and the target cells and the resultant cytotoxicity. Again, to modulate the activation or interaction means to alter the activation or interaction. As an example, the modulation of the activation might affect the intensity or the duration of the activation.

Figure 1:
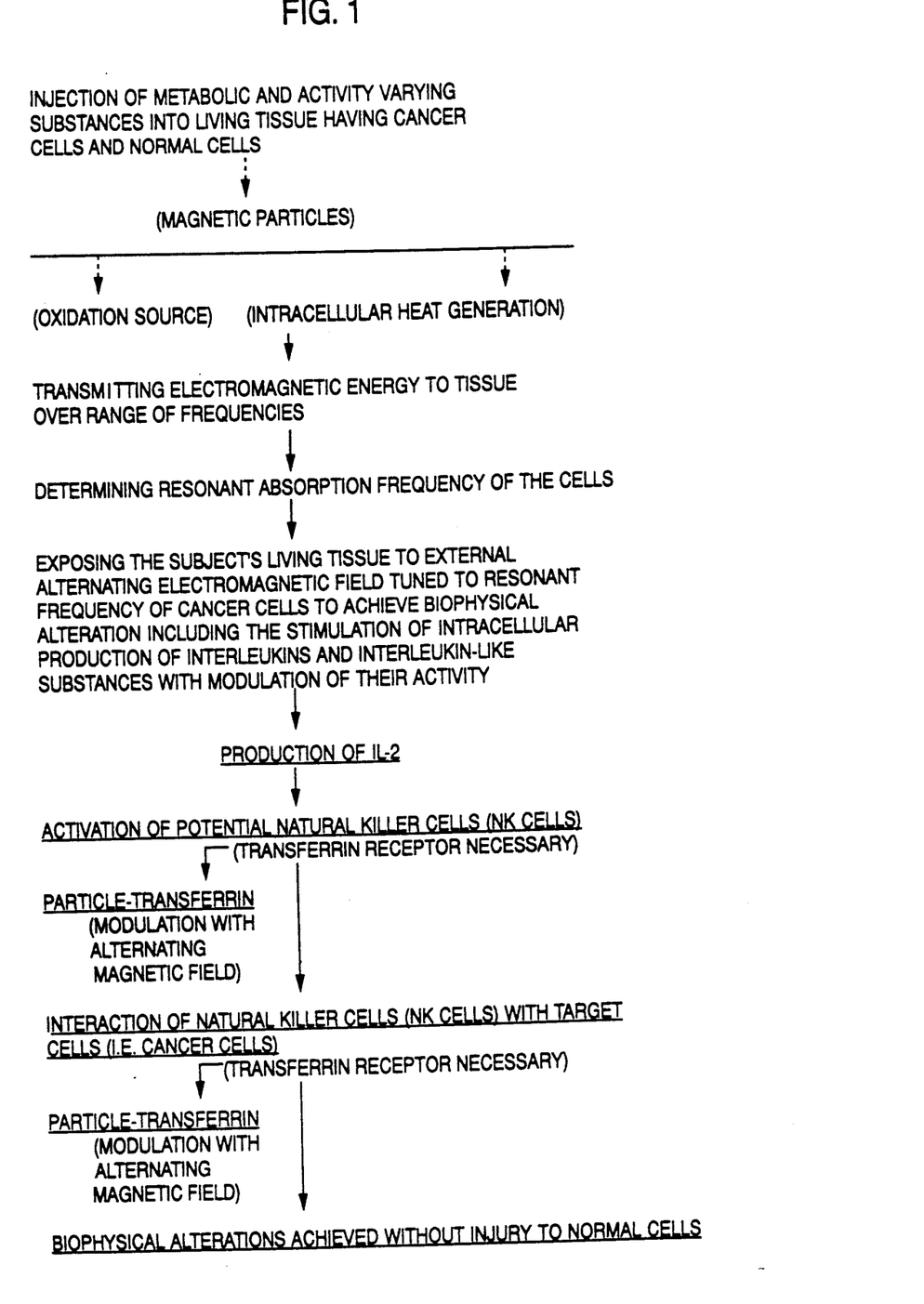
FIG. 1 is a flow chart illustrating a method of the present invention for achieving biophysical alterations in a subject without injuring his normal cells.

These processes may also be used in the same manner to affect the activated cells' ability to destroy infectious agents, and reference is hereby made to the process(es) illustrated in the flow chart of FIG. 1.

The intracellular absorption of agents other than magnetically excitable particles, i.e. various sugars, agents affecting cyclic-AMP, material or materials capable of generating heat intracellularly by chemical reaction and/or the application of an increased oxygen supply to the cells resulting in an increased rate of chemical reaction and increased intracellular metabolism, can also be utilized to alter the magnetic susceptibility of the cell and to help the absorption of energy at the cancer or other diseased cell's resonant frequency. The intracellular production of interleukins and other immunological agents is also stimulated with modulation of their activities. The intracellular absorptions enhance the difference in the resonant frequencies between the cancer and other diseased cells and the normal cells as well as affect the magnetic susceptibility of the cell thereby enhancing the processes of this invention to selectively destroy cancer and other diseased cells.

The cancer and other diseased cells and the normal cell metabolic rate and activity are affected differently by agents, such as sugars, interleukins and agents affecting cyclic-AMP, as well as by the intracellular resonant energy changes themselves. This differential response to the cancer and other diseased cells and normal cells metabolic activity allows for a variation with time in the respective resonant frequencies of the cancer and other diseased cells and the normal cells. These differences can be utilized in choosing the specific time when the resonant frequencies of the cancer or other diseased cells and the normal cells differ the most so as to enhance the process of detecting cancer and other diseased cells and the process of selectively killing the cancer and other diseased cells without injuring the normal cells and tissues. Again reference is made to the methods illustrated in the flow chart of FIG. 1.

In contrast, the steps recited in U.S. Pat. No. 4,622,952 do not inherently result in IL-2 production and/or modulation of its activities. The precise processes disclosed herein as to frequency, field strength, and so forth may be altered depending upon whether it is the production of interleukins or the modulation of their activity which is desired. Therefore, the desired effect is achieved only if the parameters are appropriate. The definition of some of these parameters, such as the use of transferrin-$Fe_3O_4$ particles, is provided herein. Depending on the desired result, a different particle may be appropriate. As an example, to affect the production of IL-2, the transferrin-$Fe_3O_4$-dextran particle is excellent. Also, to modulate the activity, particles such as transferrin-FeOOH-dextran or rhodamine-123-$Fe_3O_4$ may be used. Thus, the subject invention describes an approach to affect the production of interleukin by specific cell types. It also describes a means of modulating the interaction of the interleukin by specific cell types. It further describes a means of modulating the interaction of interleukin with the other cells so that the alterations which are produced can be modified. One means of performing this alteration is through the interaction of the IL-2 receptor and the transferrin receptor (TRF) in the cell.

EXAMPLE I

Determination of resonant energy absorption frequency for materials or tissues is obtained by using a high frequency signal generator which is capable of sweeping the frequency range to be scanned and which is connected to an antenna. A receiving coil connected to a power meter, to measure the power received, is placed a short distance away. The material or tissues, whose resonant absorption frequency is to be determined, are placed in the space between the transmitting antenna and the receiving coil. Appropriate shielding is placed laterally around the specimens being tested in such a manner that any RF energy being transmitted from the antenna to the receiving coil must pass through the specimen. As the frequency range of the signal generator is scanned and the power received by the coil is measured, the resonant absorption frequency for the specimen being tested will be indicated by a significant drop in the power received by the receiving coil, since at this resonant frequency the specimen will be absorbing some of the power.

This method is applicable to determining different resonant absorption frequencies for cancer and other diseased cells, for normal cells and for the various additive materials. The method can also be useful in measuring the alteration of the resonant absorption frequency by the intracellular absorption of various materials and by changes in the intracellular metabolic rate.

EXAMPLE II

As a specific example of a simple form of the present invention, prior to treatment, tumor tissue biopsies are taken and examined under light microscopy to confirm tumor cell identification. Two cubic centimeters of an aqueous colloidal solution of FeOOH and dextran are injected intravenously into the subject. This solution when injected intravenously is capable of being intracellularly absorbed and thus greatly increases the magnetic susceptibility of the intracellular structure of the cell. Moreover, after this solution has been intracellularly absorbed, it is capable of being metabolized by the cell thereby producing a variable magnetic susceptibility with reference to time. Biopsies taken several hours after the intravenous injection of the solution and examined under electron microscopy confirm the intracellular absorption of this solution, particularly by the cancer cells. Biopsies of cancer tissue and normal tissue taken at one hour, two hours, four hours, twelve hours, twenty-four hours, and forty-eight hours after the intravenous injection of this solution are immediately frozen and subsequently taken for measurements of magnetic susceptibility in a Vibrating Sample Magnetometer, Princeton Applied Research Model No. 159. Using this data, it is possible to plot the rise in magnetic susceptibility due to the intracellular absorption of the solution in the cancer cells and to compare it to the magnetic susceptibility changes in the normal cells. This gives data on the increase in magnetic susceptibility not only due to the intracellular absorption of the solution, but also with reference to the metabolism in the time period. Using frozen samples from a time period which indicates high relative magnetic susceptibility of cancer cells to normal cells, and using the method described herein in Example I, for determining the optimal resonant absorption frequency, it was determined that a high frequency electromagnetic field of 450 kilohertz applied approximately four hours after the intravenous injection of this solution would provide optimal resonant energy absorption and resultant biophysical alterations by the cancer cells. Approximately forty-eight hours after this procedure was followed, biopsies were taken and examined under light microscopy and electron microscopy, and these biopsies confirmed the effectiveness of this procedure in destroying cancer cells without injuring surrounding normal cells and normal tissue.

EXAMPLE III

Figure 3:
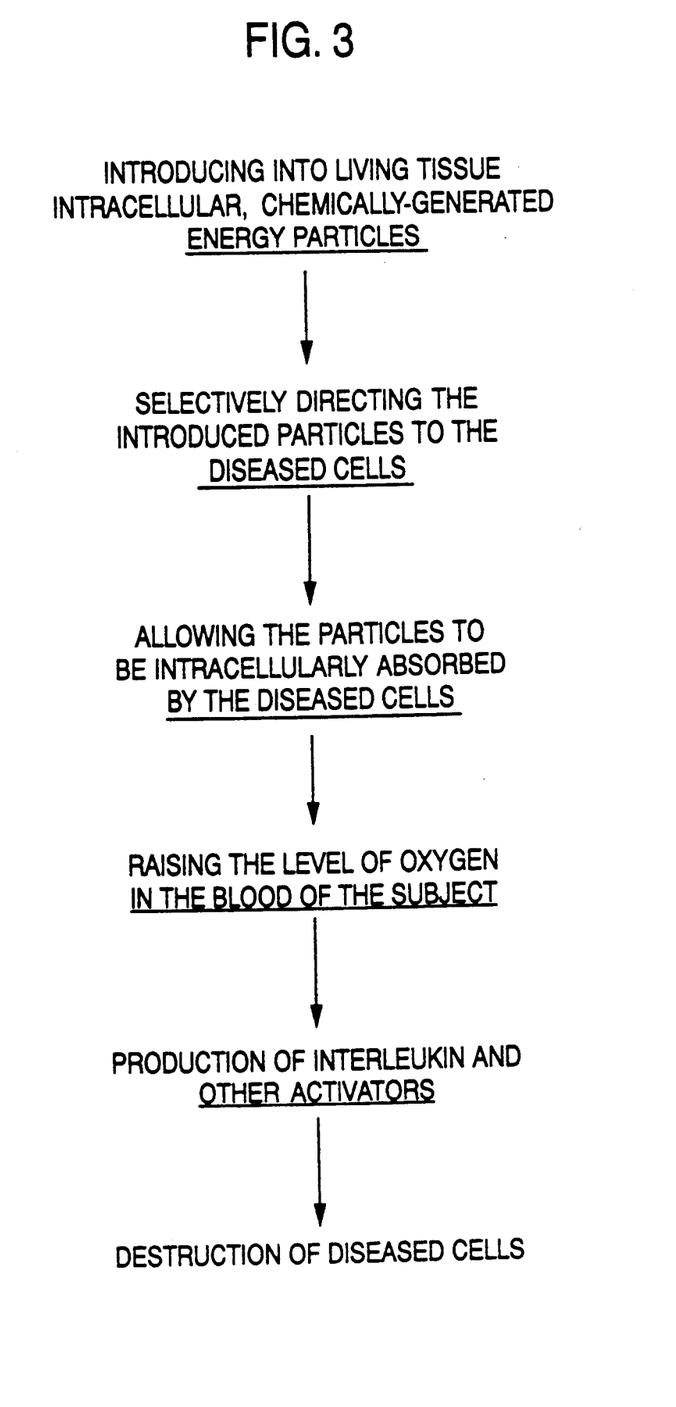
FIG. 3 is a flow chart illustrating a method of the present invention for treating diseased cells in a subject, including the step of raising the level of oxygen in the subject's blood.

Basically this invention relates to processes for achieving biophysical alterations in the intracellular structure of living cells, particularly cancer and other diseased cells, such as atherosclerotic and infectious cells, by raising the energy level inside the cells, intracellularly. The application of energy derived from chemical reaction can be utilized for this purpose. Intracellularly chemically-generated, energy particles (which are particles created in the cell by reaction mechanisms and capable of generating energy in the cell) are first introduced into the subject. After the particles have been absorbed by the diseased cells, as by waiting for more than an hour after introducing the particles, the oxygen level in the subject is increased. A flow chart illustrating this method is provided in FIG. 3.

As a specific example, ferric oxyhydroxide particles of 0.7 micron size are colloidally suspended in a five percent dextrose aqueous solution in an amount of approximately fifty milligrams of the particles per cubic centimeter. Dosages in the amount of thirty milligrams per kilogram of body weight of the subject are intravenously injected into the subject. Techniques described in U.S. Pat. No. 4,106,488 can be employed to more selectively direct the particles to the cancer or other diseased cells. The particles can be specifically directed to the cell by a number of mechanisms depending upon the ultimate goal. As an example, the receptor mechanism can be utilized to localize certain specific particles.

Approximately four hours after injection, the particles will have been intracellularly absorbed by the cancer or other diseased cells. The subject is then placed in a hyperbaric oxygen chamber and subjected to an approximate fifty percent oxygen concentration at a pressure of three atmospheres and for a period of approximately three hours. Normal hyperbaric chamber safety procedures in achieving compression and decompression would be followed.

The hyperbaric oxygen chamber procedure raises the oxygen level of the subject's blood which, in turn, raises the rate of intracellular absorption of oxygen. The increased rate of intracellular oxygen absorption, especially by the cancer and other diseased cells, coupled with the already intracellularly absorbed ferric oxyhydroxide particles, result in an increased rate of oxidation and metabolism of the ferric oxyhydroxide and therefore in a significant rise of intracellular energy. This significant rise of intracellular energy further results in intracellular thermal changes, stimulates the intracellular production of interleukins and other activators, and affects their activity resulting in the destruction of cancer and other diseased cells wherever they exist in the subject. This term "other activators" describes any agent which can alter the process of intracellular events. Examples thereof include other interleukins, interferons and prostaglandins.

Other particles of this invention which can be used are the particles involved in receptor mechanisms, including $Fe_3O_4$-transferrin-dextran, transferrin-FeOOH-dextran, rhodamine-123-$Fe_3O_4$, LDL-$Fe_3O_4$, and LDL-transferrin-$Fe_3O_4$ particles. This receptor mechanism for particle localization involves a number of methods. As an example in cancer cells, the increased expression of transferrin receptors allows $Fe_3O_4$-transferrin-dextran particles to localize the particles to the cancer cell. With respect to atherosclerotic lesions the low-density lipoprotein (LDL) receptor on the diseased cells is able to localize the LDL-transferrin-$Fe_3O_4$ particle to the diseased cells.

This process thereby alters the intracellular metabolism and raises the energy level in the cell. This in turn affects the magnetic susceptibility, and this change in magnetic susceptibility affects the absorption of energy at a given frequency. Accordingly, an alternating electromagnetic field can then also be applied, and the resonant frequency is altered in order to affect the diseased cells and minimize any effect on normal cells.

EXAMPLE IV

In another example the subject is placed on a table with an electromagnetic energy transmitter on one side thereof and a detection receiver on the opposite side. The transmitter and the receiver are on a moveable axis which can rotate 360° and move laterally the length of the subject. The frequency of the transmitter is varied from one kilohertz to fifty megahertz at each point on the 360° circle. The input from the detection receiver is fed into a computer which composes a three-dimensional picture of the resonant frequencies of all points in the subject. The distribution of cancer and other diseased cells is noted as is their resonant frequency.

The subject is then placed in a large coil approximately three to six feet in diameter, and the coil is energized at the frequency determined by the computer. The subject is then treated for an increment of time determined from computer data. This increment of time can range from two to thirty minutes. Approximately forty-eight hours later, the subject is placed back on the original table and the procedure of detection repeated. If any cancer or other diseased cells with their specific resonant frequency are detected, the subject is treated again, and so forth.

EXAMPLE V

As another specific example of the present invention, $Fe_3O_4$-Transferrin particles in a concentration of eight mg/cc at a dose of 0.01A 1mg/kg are injected intravenously into the subject over a period of thirty minutes. After twelve hours the subject is exposed for three minutes to an alternating electromagnetic field, which includes energy with variable frequency in the range of 1 kilohertz to 50 megahertz, at 450 kilohertz or the desired resonant absorption frequency. IL-2 is thereby produced and proceeds to (1) activate NK cells which in turn (2) interact with their target (cancer or other diseased) cells. The transferrin ($Fe_3O_4$-Transferrin) particle attaches to the TFR at the NK cell with the target cell. Through the use of the alternating electromagnetic field these processes can be controlled. Therefore the production of IL-2, the activation of the NK cells and the interaction of the NK cells with the target cells can all be controlled. Since it is thought that NK cells in certain instances recognize the target cells by the TRF on the target cells, the transferrin particles can easily affect the interaction between the NK cells and the target cells and so forth.

Figure 2:
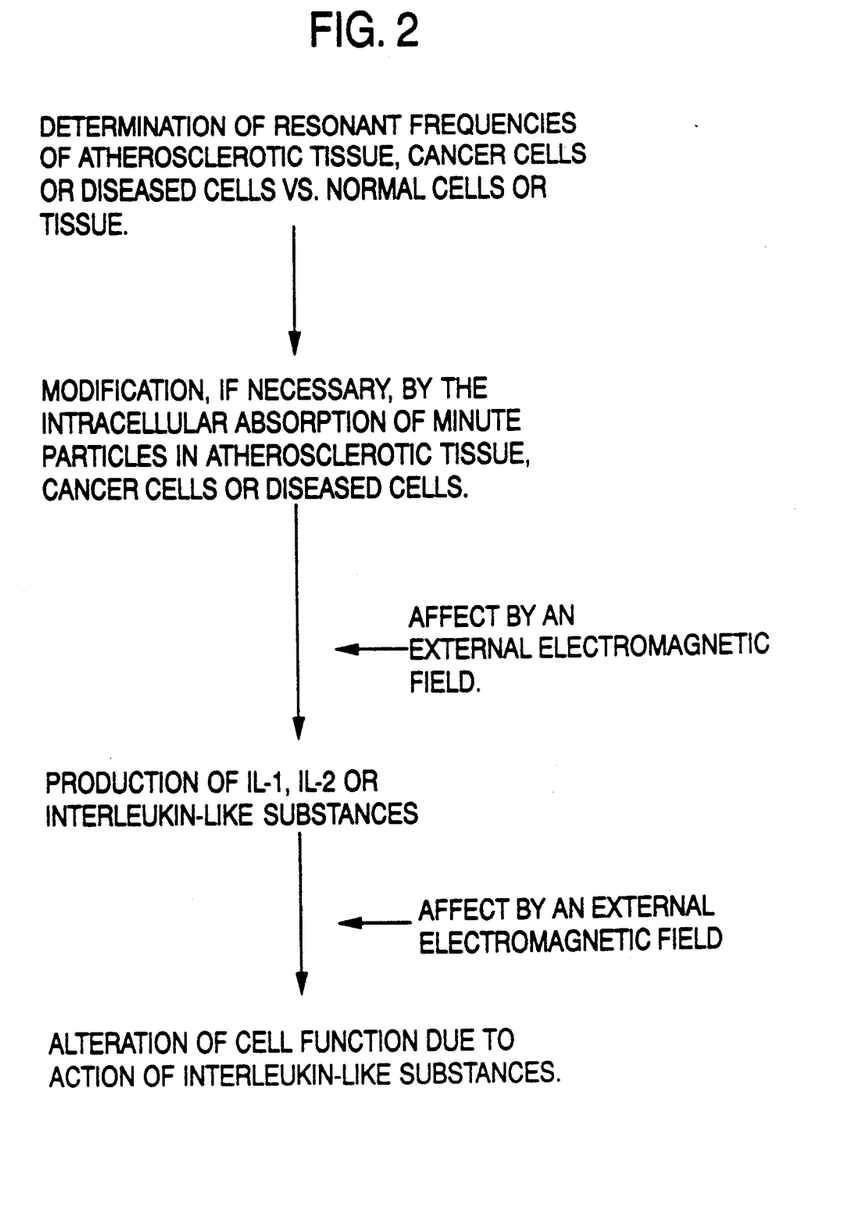
FIG. 2 is a flow chart illustrating a method of this invention for altering cell function by the action of interleukin-like substances.

A variation of the example of the paragraph above is to introduce into the subject particles which are ferromagnetic, paramagnetic or diamagnetic and which integrate with the interaction between interleukin and the target cells. An example of such particles are $Fe_3O_4$-Transferrin particles. These particles can be introduced by intravenously injecting a solution of them in a concentration of 0.1 mg/cc to 100 mg/cc, or for example eight mg/cc, and in a dose of 0.001 mg/kg to 100 mg/kg, or for example 1 mg/kg, into the subject over a period of thirty minutes. An alternating electromagnetic field having a variable frequency in the range of 1 kilohertz to 50 megahertz and a field strength of 50 gauss to 500 kilogauss is generated. The generated field is tuned to 450 kilohertz or the desired resonant absorption frequency of the diseased cells (as previously explained). Roughly twelve hours after introducing the particles into the subject he is exposed to the tuned field for a period of one to thirty minutes, or for example three minutes. As stated above, IL-2 is thereby produced and it proceeds to activate the NK cells which in turn interact with their target cells, and so forth. These processes can be controlled by altering the field strength, frequency and timing, as can be better understood by referring to the flow chart of FIG. 2 herein. In other words, the method illustrated in that flow chart can be altered depending upon the desired and result.

In addition to treating cancer cells, this method can be applied in a variety of other diseases whose processes involve the interaction of interleukins and target cells. Atherosclerosis, infectious diseases, and rheumatoid arthritis are examples of such diseases.

These methods of the present invention which use alternating electromagnetic fields and intracellular products to modulate the interaction of IL-2 and the cells to be activated (such as NK cells), and the interaction of NK cells and target (cancer or other diseased) cells are unique. Other known methods of stimulating IL-2 production are not capable of controlling the effect of IL-2 on the other cells and the interaction of cells via the mechanisms discussed herein. Therefore, not only is the IL-2 production controlled, but after the production, the function is also controlled.

EXAMPLE VI

The resonant absorption frequencies of the lymphocytes, monocytes and macrophages, as well as that of the normal cells, of the subject are determined by any of the processes which are well known in the art and/or are described herein. ("Normal cell" as used herein describes cells which are not immunologically capable of being altered. The term "normal" is used since the lymphocytes, monocytes and macrophages undergo alterations to produce IL-2 and/or interleukin-like substances.) Metabolic and activity-varying substances are intravenously injected into the tissue of the subject to alter the biophysical characteristics of the intracellular structure of the subject's (living) cells, such as the lymphocytes, monocytes and macrophages. The biophysical characteristics can include the magnetic susceptibility of the intracellular structure and therefore the resonant energy absorption frequency of the living cell, or the lymphocytes, monocytes and macrophages. Also, activity-varying substances include any of the substances which can change the activity of the cells or the subcellular systems. Examples thereof include interferons, lymphocyte activation factors, prostaglandins and steroids. The dosage to be used of these substances varies. These substances can be introduced either prior to, during, or after treatment depending on which portion of the cycle is to be affected. These substances, if introduced before or during the energy absorption step, may alter the absorption frequencies. The entire process however can occur as described in this example, since the frequency tuning steps allow for these alterations.

The subject is placed either entirely (or partially) in a helical coil capable of generating an electromagnetic field which includes energy with variable frequency in the range of 1 kilohertz to 50 megahertz, for example. The electromagnetic field is tuned to the desired frequency within that range and the subject thereby exposed to the tuned field. The desired frequency can be that which is (1) closest to the resonant absorption frequencies of the lymphocytes, monocytes and macrophages and furthest from the resonant frequencies of the normal cells, or (2) simply a resonant absorption frequency of the lymphocytes, monocytes and macrophages. The exposure of the subject to the tuned field achieves biophysical alterations in the subject including stimulating the intracellular production of interleukins, such as IL-2, and/or interleukin-like substances (via the usual endoplasmic reticulum-ribosomal-RNA pathway) and modulating their activity. The alteration can be in the intracellular structures of the lymphocytes, monocytes and macrophages, and can include the intracellular heat rise of the lymphocytes, monocytes and macrophages. Modulating their activity means, for example, altering the behavior of interleukin or IL-2 or other cells. Additionally, "interleukin-like substances" are any of the substances like IL-1 or IL-2 which are capable of modifying cellular behavior and function.

Figure 4:
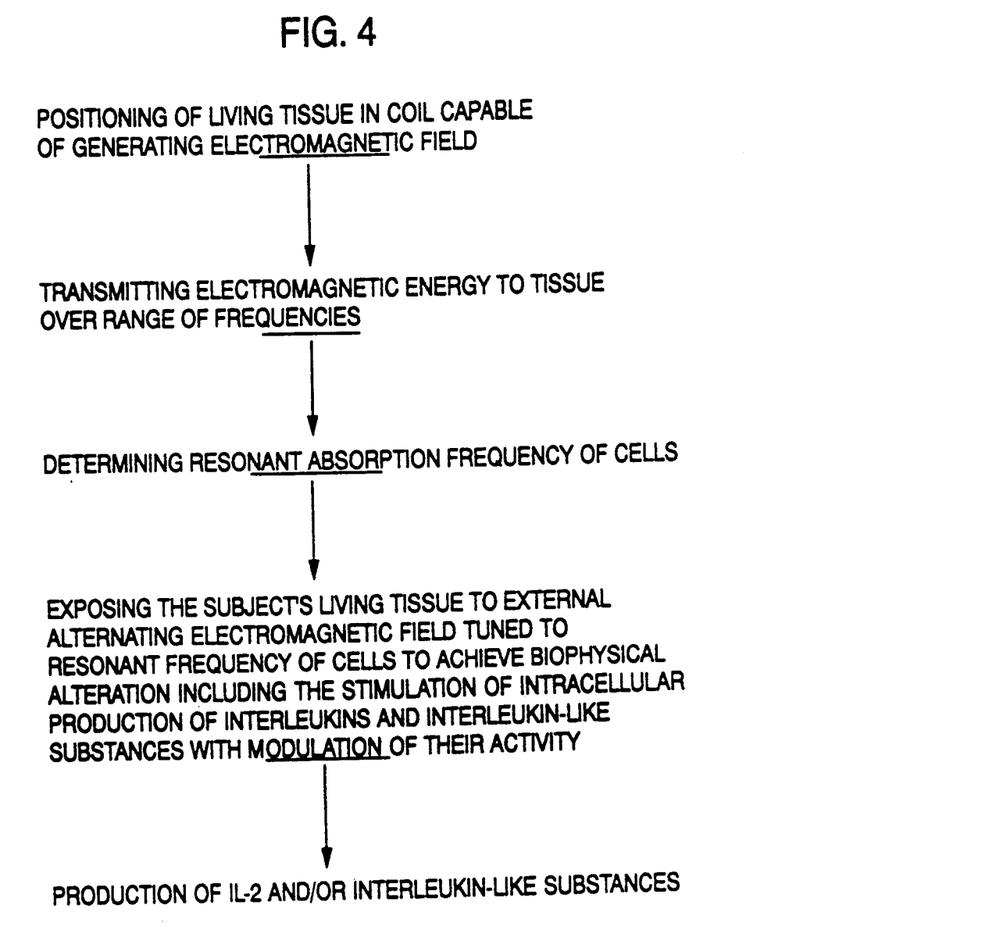
FIG. 4 is a flow chart illustrating (in a simplified form) a method of the present invention for producing Il-2 and/or interleukin-like substances.

The exposure to the tuned field causes the production intracellularly of interleukin and IL-2 through the interaction of the field and the intracellular particles and/or the interaction of the field and the cell components, themselves. These cell components include membranes, mitochondria and components of the cell capable of responding to the field. A method of this example is illustrated in simplified form by the flow chart of FIG. 4.

This process for producing IL-2 and/or interleukin-like substances can be enhanced by introducing intracellular, chemically-generated energy substances which are taken up intracellularly. These introduced substances stimulate the intracellular production of IL-2 and the interleukin-like substances and modulate their activity. Examples of these energy substances include glucose derivatives and 2-deoxyglucose, as well as phosphorous compounds, i.e. cyclic AMP. Once again, these can be introduced at the desired time during the process.

From the foregoing detailed description, it will be evident that there are a number of changes, adaptations and modifications of the present invention which come within the province of those persons having ordinary skill in the art to which the aforementioned invention pertains. However, it is intended that all such variations not departing from the spirit of the invention be considered as within the scope thereof as limited solely by the appended claims.

What is claimed is:

1. A process for treating diseased cells in living tissue of a subject comprising the steps of:
   introducing into the living tissue of the subject intracellular, chemically-generated energy particles;
   allowing said introduced particles to be intracellularly absorbed by the diseased cells;
   thereafter, raising the level of oxygen in the blood of the subject and thereby stimulating the intracellular production of interleukins and other activators, and thereby destroying the diseased cells; and
   after said raising step, applying to the subject an alternating electromagnetic field tuned to a resonant frequency of the diseased cells.

2. The process of claim 1, including,
   said introducing step including selectively directing said particles to the diseased cells.

3. The process of claim 2 including,
   said directing step including utilizing receptor mechanism in the subject and thereby localizing said particles in the diseased cells.

4. The process of claim 1 including,
   said introducing step including intravenously injecting said particles into the subject.

5. The process of claim 1 including,
   said raising step including subjecting the subject to an increased oxygen concentration.

6. The process of claim 6 including,
   said subjecting step including placing the subject in a hyperbaric oxygen chamber.

7. The process of claim 1 including,
   said raising step including placing the subject in a hyperbaric oxygen chamber and subjecting the subject therein to an approximate fifty percent oxygen concentration at a pressure of approximately three atmospheres for approximately three hours.

8. The process of claim 1 including,
   said raising the oxygen level step including subjecting the subject to hyperbaric air.

9. The process of claim 1 including,
   said raising the oxygen level step including subjecting the subject to hyperbaric oxygen.

10. The process of claim 1 including, said allowing step including waiting a period greater than one hour after completing said introducing step before commencing said raising step.

11. The process of claim 10 including,
said allowing step including said waiting period being approximately four hours.

12. A process for treating diseased cells in living tissue of a subject comprising the steps of:
introducing into the living tissue of the subject a solution of ferric oxyhydroxide particles;
allowing said introduced particles to be intracellularly absorbed by the diseased cells; thereafter, raising the level of oxygen in the blood of the subject and thereby stimulating the intracellular production of interleukins and other activators, and thereby destroying the diseased cells; and
after said raising step, applying to the subject an alternating electromagnetic field tuned to a resonant frequency of the diseased cells.

13. The process of claim 12 including,
said introducing step including selectively directing said particles to the diseased cells.

14. The process of claim 12 including,
said introducing step including intravenously injecting said particle solution into the subject.

15. The process of claim 12 including,
said raising step including placing the subject in a hyperbaric oxygen chamber.

16. A process for treating cancer cells in living tissue of a subject comprising the steps of:
introducing into the living tissue of a subject $Fe_3O_4$-transferrin-dextran particles;
allowing said introduced particles to be intracellularly absorbed by the cancer cells; and
thereafter, raising the level of oxygen in the blood of the subject and thereby stimulating the intracellular production of at least one of interleukins and other activators, and thereby destroying the cancer cells.

17. The process of claim 15 including,
said introducing step including intravenously injecting a solution of said particles into the subject.

18. The process of claim 16 including,
said raising step including placing the subject in a hyperbaric oxygen chamber.

19. The process of claim 19 including,
after said raising step, applying to the subject an alternating electromagnetic field tuned to a resonant frequency of the cancer cells.

20. A process for treating atherosclerotic cells in living tissue of a subject comprising the steps of:
introducing into living tissue of a subject LDL-transferrin-$Fe_3O_4$ particles;
allowing said introduced particles to be intracellularly absorbed by the atherosclerotic cells; and
thereafter, raising the level of oxygen in the blood of the subject and thereby stimulating the intracellular production of at least one of interleukins and other activators, and thereby destroying the atherosclerotic cells.

21. The process of claim 20 including,
said introducing step including intravenously injecting a solution of said particles into the subject.

22. The process of claim 20 including,
said raising step including subjecting the subject to hyperbaric oxygen in a hyperbaric oxygen chamber.

23. The process of claim 20 including,
after said raising step, applying to the subject an alternating electromagnetic field tuned to a resonant frequency of the atherosclerotic cells.

24. A process for treating diseased cells in living tissue of a subject comprising the steps of:
introducing into the living tissue of the subject intracellular, chemically-generated energy particles, said particles including ferric oxyhydroxide particles;
allowing said introduced particles to be intracellularly absorbed by the diseased cells;
thereafter, raising the level of oxygen in the blood of the subject and thereby stimulating the intracellular production of interleukins and other activators, and thereby destroying the diseased cells; and
after said raising step, applying to the subject an alternating electromagnetic field tuned to a resonant frequency of the diseased cells.

25. The process of claim 24 including,
said introducing step including selectively directing said particles to the diseased cells.

26. The process of claim 25 including,
said directing step including utilizing receptor mechanism in the subject and thereby localizing said particles in the diseased cells.

27. The process of claim 24 including,
said raising step including placing the subject in a hyperbaric oxygen chamber and subjecting the subject therein to an approximate fifty percent oxygen concentration at a pressure of approximately three atmospheres for approximately three hours.

28. The process of claim 24 including,
said allowing step including waiting a period greater than one hour after completing said introducing step before commencing said raising step.

29. The process of claim 28 including,
said allowing step including said waiting period being approximately four hours.

30. A process for treating cancer cells in living tissue of a subject comprising the steps of:
introducing into the living tissue of the subject intracellular, chemically-generated energy particles;
allowing said introduced particles to be intracellularly absorbed by the cancer cells;
thereafter, raising the level of oxygen in the blood of the subject and thereby stimulating the intracellular production of interleukins and other activators, and thereby destroying the cancer cells; and
after said raising step, applying to the subject an alternating electromagnetic field tuned to a resonant frequency of the cancer cells.

31. The process of claim 30 including,
said introducing step including selectively directing said particles to the cancer cells.

32. The process of claim 31 including,
said directing step including utilizing receptor mechanism in the subject and thereby localizing said particles in the cancer cells.

33. The process of claim 30 including,
said raising step including placing the subject in a hyperbaric oxygen chamber and subjecting the subject therein to an approximate fifty percent oxygen concentration at a pressure of approximately three atmospheres for approximately three hours.

34. The process of claim 30 including, said allowing step including waiting a period greater than one hour after completing said introducing step before commencing said raising step.

35. The process of claim 34 including,
said allowing step including said waiting period being approximately four hours.

36. A process for treating diseased cells in living tissue of a subject comprising the steps of:
introducing into the living tissue of the subject intracellular, chemically-generated energy particles, said particles being ferric oxyhydroxide particles of 0.7 micron size colloidally suspend in a five percent dextrose aqueous solution in an amount of approximately fifty milligrams of particles per cubic centimeter of solution;
allowing said introduced particles to be intracellularly absorbed by the diseased cells;
thereafter, raising the level of oxygen in the blood of the subject and thereby stimulating the intracellular production of interleukins and other activators, and thereby destroying the diseased cells; and
after said raising step, applying to the subject an alternating electromagnetic field tuned to a resonant frequency of the diseased cells.

37. The process of claim 36 including,
said introducing step including selectively directing said particles to the diseased cells.

38. The process of claim 37 including,
said directing step including utilizing receptor mechanism in the subject and thereby localizing said particles in the diseased cells.

39. The process of claim 36 including,
said introducing step including intravenously injecting said particle solution into the subject.

40. The process of claim 36 including,
said introducing step including intravenously injecting into the subject said particle solution in a dosage of about thirty milligrams per kilogram of body weight of the subject.

41. The process of claim 36 including,
said raising step including placing the subject in a hyperbaric oxygen chamber and subjecting the subject therein to an approximate fifty percent oxygen concentration at a pressure of approximately three atmospheres for approximately three hours.

42. The process of claim 36 including,
said allowing step including waiting a period greater than one hour after completing said introducing step before commencing said raising step.

43. The process of claim 42 including,
said allowing step including said waiting period being approximately four hours.

44. A process for treating diseased cells in living tissue of a subject comprising the steps of:
introducing into the living tissue of the subject intracellular, chemically-generated energy particles, said particles being selected from the group of $Fe_3O_4$-transferrin-dextran, transferrin-FeOOH-dextran, rhodamine-123-$Fe_3O_4$, LDL-$Fe_3O_4$, and LDL-transferrin-$Fe_3O_4$ particles;
allowing said introducing particles to be intracellularly absorbed by the diseased cells; and
thereafter, raising the level of oxygen in the blood of the subject and thereby stimulating the intracellular production of interleukins and other activators, and thereby destroying the diseased cells.

45. The process of claim 44 including,
said introducing step including selectively directing said particles to the diseased cells.

46. The process of claim 45 including,
said directing step including utilizing receptor mechanism in the subject and thereby localizing said particles in the diseased cells.

47. The process of claim 44 including,
said raising step including placing the subject in a hyperbaric oxygen chamber and subjecting the subject therein to an approximate fifty percent oxygen concentration at a pressure of approximately three atmospheres for approximately three hours.

48. The process of claim 44 including,
said allowing step including waiting a period greater than one hour after completing said introducing step before commencing said raising step.

49. The process of claim 48 including,
said allowing step including said waiting period being approximately four hours.

50. The process of claim 44 including,
after said raising step, applying to the subject an alternating electromagnetic field tuned to a resonant frequency of the diseased cells.

* * * * *